United States Patent [19]
Helmlinger et al.

[11] 3,948,816
[45] Apr. 6, 1976

[54] MERCAPTO CARBOXYLIC ACID ESTERS

[75] Inventors: Daniel Helmlinger, Dubendorf; Dietmar Lamparsky, Wangen-Dubendorf; Peter Schudel, Grut; Trudi Sigg-Grütter, Winterthur; Jost Wild, Zurich, all of Switzerland

[73] Assignee: Givaudan Corporation, Clifton, N.J.

[22] Filed: Mar. 28, 1974

[21] Appl. No.: 455,761

Related U.S. Application Data

[62] Division of Ser. No. 223,044, Dec. 2, 1971, abandoned.

[52] U.S. Cl. .............................................. 252/522
[51] Int. Cl.² ........................ A61K 7/46; C11B 9/00

[58] Field of Search .................. 252/522; 260/481 R

[56] References Cited
UNITED STATES PATENTS
3,277,143   10/1966   Tilles ............................. 260/481 R FOREIGN PATENTS OR APPLICATIONS
542,641   1/1942   United Kingdom ................ 260/481
805,761   5/1951   Germany ........................... 260/481

*Primary Examiner*—C. Davis
*Attorney, Agent, or Firm*—Thomas Cifelli, Jr.

[57] ABSTRACT

There are disclosed novel β-mercapto carboxylic acid esters and methods of producing the same. These novel esters are useful as odorants and flavorants.

4 Claims, No Drawings

MERCAPTO CARBOXYLIC ACID ESTERS

This is a division of application Ser. No. 223,044, filed Dec. 2, 1971, and now abandoned.

SUMMARY OF THE INVENTION

The present invention is concerned with new β-mercapto carboxylic acid esters of the general formula

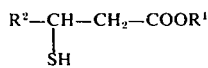

$$R^2-CH-CH_2-COOR^1 \quad\quad\quad I$$
$$\phantom{R^2-CH-}|$$
$$\phantom{R^2-CH-}SH$$

wherein $R^1$ signifies alkyl of 1–6 carbon atoms, alkenyl of 2–6 carbon atoms of alkadienyl of 4–6 carbon atoms and $R^2$ signifies an alkyl or alkenyl residue containing 3–9 carbon atoms, a process for the manufacture of these new esters, as well as their use as odorants and/or flavorings and odorant and/or flavoring compositions with a content of such esters.

The new β-mercapto carboxylic acid esters of General Formula I can be manufactured in accordance with the invention by reacting an α,β-unsaturated carboxylic acid ester of the general formula

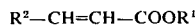

$$R^2-CH=CH-COOR^1 \quad\quad\quad II$$

wherein $R^1$ and $R^2$ have the above significance with hydrogen sulphide in the presence of a basic catalyst.

DESCRIPTION OF THE PREFERRED EMBODIMENTS

The alkyl, alkenyl and alkadienyl groups consisting the moieties of $R^1$ and $R^2$ in Formula I above can be unbranched or branched and, insofar as they contain double bonds, exist in any desired stereo configuration. Examples of such groups are methyl, ethyl, n-propyl, iso-propyl, n-butyl, isobutyl, sec. butyl, tert.-butyl, n-pentyl, isoamyl, 3-pentyl[-CH(CH$_2$CH$_3$)$_2$], n-hexyl; allyl, dimethallyl, hexen-(2)-yl, hexen-(3)-yl (cis or trans): hexadien-(2,4)-yl, hepten-(1)-yl and the like.

Especially preferred are the compounds of General Formula I-1

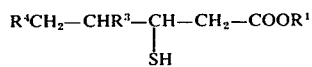

$$R^4CH_2-CHR^3-CH-CH_2-COOR^1 \quad\quad I\text{-}1$$
$$\phantom{R^4CH_2-CHR^3-CH-}|$$
$$\phantom{R^4CH_2-CHR^3-CH-}SH$$

wherein $R^1$ has the above significance and is preferably unbranched, $R^3$ signifies hydrogen or alkyl containing 1–3 carbon atoms and $R^4$ signifies alkyl, preferably unbranched, containing 1–7 carbon atoms.

Formulae I and I-1 are meant to include all optically active and racemic forms which are possible on the basis of asymmetric centres which are present.

Examples of compounds of General Formula I in accordance with the invention are:

3-mercapto-4-methyl (or ethyl)-caproic acid esters such as the methyl, ethyl, the hexen-(2)-yl, the cis-hexen-(3)-yl or the hexadien-(2,4)-yl ester;

3-mercapto-caproic acid esters such as the methyl or ethyl ester;

3-mercapto-octanoic acid methyl or ethyl ester;
3-mercapto-nonanoic acid methyl or ethyl ester;
3-mercapto-decanoic acid methyl or ethyl ester.

The reaction of the α,β-unsaturated carboxylic acid esters II with H$_2$S can be carried out according to methods which are known per se, suitably the reaction mixture is cooled to below the boiling point of hydrogen sulfide preferably to about −30° to −40°C and hydrogen sulfide, which had previously been condensed at a lower temperature suitably around −80°C, is decanted into the reaction mixture. Although the reaction can be carried out solvent-free and without the application of pressure, as a rule it is expedient to use a solvent (e.g. an ether or an alcohol) and to allow the reaction to take place in closed vessel (autoclave) in order to avoid losses of H$_2$S.

The sealed autoclave is permitted to warm to ambient temperature and then further warmed to a temperature from about 60° to about 90°C from about 1 to about 5 hours. The course of reaction may be observed by following the pressure drop of the pressure in the autoclave. Initial and final pressures of course depend upon the size of the autoclave utilized and on the charge placed therein. In a typical run, reaction will start at a pressure of approximately 25 atmospheres (gauge) and drop to a pressure for about 2 to about 3 atmospheres.

As basic catalysts there can, for example be used: alkali hydroxides such as sodium or potassium hydroxide; alkaline earth hydroxides such as calcium hydroxide; alcoholates such as sodium methylate or ethylate; organic bases such as trialkylamines (e.g. triethylamine), pyridine, piperidine etc.

The α,β-unsaturated esters II employed as starting substances can, insofar as they are not known, be obtained according to methods which are known per se from the corresponding α,β-unsaturated acids by esterification with an alcohol R$^1$OH or also by re-esterification. The α,β-unsaturated acids are in turn readily accessible by Knoevenagel condensation of a corresponding aldehyde with malonic acid diethyl ester and subsequent saponification and decarboxylation.

The compounds of General Formula I and, among them, particularly 3-mercapto-4-methyl-caproic acid methyl ester are distinguished by particular diffuse green notes with fruity impact which readily combine with known fragrance notes such as lavender, chypre, gardenia, jasmine and rose and lead to novel interesting modifications of such floral bases. On the basis of these olfactory qualities, surprising for sulphur-containing compounds, the compounds of General Formula I can be used as odorants and/or flavorings, for example in perfumery for the manufacture of odorant compositions such as perfumes, or for perfuming products of all kinds such as washing agents, detergents, soaps and other cosmetic articles, or for aromatizing foodstuffs and delicacies as well as of beverages. In odorant compositions, very good head note effects are achieved with additions of less than 0.01%. However, in order to achieve certain modifications higher concentrations, for example of 0.05–1% can also be used. In aromatized foodstuffs the concentrations can, for example, lie between 0.01 and 100 PPM, preferably between 0.1 and 10 PPM.

In the following Examples, the temperatures are stated in degrees centigrade.

EXAMPLE 1

50 g of 4-methyl-2-hexenoic acid ethyl ester are placed in an autoclave with 0.5 g of hydroquinone and a solution of 2 g of sodium hydroxide in 50 ml of absolute ethanol. The autoclave is subsequently cooled to −30° to −40° and a hydrogen sulphide amount of 60 ml previously condensed in another vessel at −78° is decanted into the autoclave. The autoclave is immediately sealed and, after reaching room temperature, placed into a warm (80°) oil-bath. The reaction mixture is left for 2 hours at an internal temperature of 70°, the pressure of on average 25 atm. (gauge) initially reached falling by 2 to 3 atm. After completed reaction, the autoclave is cooled, the excess pressure released, the reaction mixture (after opening the autoclave) taken up in ether and the ether solution washed neutral and dried. After distilling off the solvent, the residue is fractionally distilled in the vacuum of the water-jet pump. There are thus obtained 47 g of 3-mercapto-4-methyl-caproic acid ethyl ester of boiling point 107°–108°/10 mm/Hg, $n_D^{20}$ 1.4593.

The very diffusively acting odour of the compound is green in the direction of a leaf green, slightly rose-like, fruity, with slightly sulphurous side-note.

EXAMPLE 2

0.2 g of sodium are dissolved in 10 ml of absolute ethyl alcohol. After completed alcoholate-formation, 5 g of 2-octenoic acid ethyl ester are added and the solution is cooled to −70°. At this temperature, 10 ml of hydrogen sulphide are condensed into the solution. Subsequently, the whole mixture is immediately transferred into an autoclave, pre-cooled to about −30°, and left by itself overnight at room temperature in the sealed pressure vessel. On the next morning, the autoclave is heated at 50° for a further 2 hours. After cooling to room temperature, the excess hydrogen sulphide is vented off, the reaction product washed with saturated common salt solution, dried and distilled. There are obtained 1.6 g of 3-mercapto-octanoic acid ethyl ester of boiling point 74°/0.4 mm Hg, $n_D^{20}$ 1.4538.

The compound smells fatty-green and possesses fruity aspects which in dilution are reminiscent of rhubarb.

EXAMPLE 3

A sodium methylate solution is freshly prepared from 0.3 g of sodium and 5 ml of methanol. 10 g of 2-nonenoic acid methyl ester are added to this solution and the mixture is cooled to −70°. After reaching this temperature, 20 ml of hydrogen sulphide are condensed in and the whole batch is transferred into a pre-cooled autoclave. The pressure-vessel is sealed and immediately heated at 50° in an oil-bath for 3 hours. The autoclave is subsequently cooled to room temperature, the excess hydrogen sulphide vented off and the reaction mixture washed with saturated common salt solution and dried. There are obtained 12.4 g of crude product which, after distillation, yields 5.7 g of pure 3-mercaptononanoic acid methyl ester of boiling point 70°/0.2 mm Hg, $n_D^{20}$ 1.4602.

The odour of the compound acts fatty-green with citronellol-like character.

EXAMPLE 4

Analogously to Example 3, from 7 g of 2-decenoic acid ethyl ester in the presence of sodium ethylate there are obtained 6.9 g of crude product which, after distillation, yields 2.3 g of 3-mercapto-decanoic acid ethyl ester of boiling point 85°/0.2 mm Hg, $n_D^{20}$ 1.4593.

The compound smells fatty-sourish, is reminiscent of enanthic ether and possesses only a weak sulphurous side-note.

EXAMPLE 5

Analogously to Example 3, from 2,4-decadienoic acid ethyl ester there is obtained 3-mercapto-4-decenoic acid ethyl ester of boiling point 88° to 90°/0.8 mm Hg. In the infra-red spectrum, the compound possesses the characteristic bands at 2580 (—SH), 1738, 1160 (—COO—) and 972 (C=C) cm$^{-1}$. The NMR spectrum likewise displays all signals for the stated structure, namely $\delta$ = 0.88 (T,J=5 cps) for CH$_3$—; 1.265 (T,J=7 cps) for CH$_3$-CH$_2$-O; 3.05 (M,2M) for CH$_2$-CO; 3.45 (M,1H) for C-CH(SH)-C; 4.17 (Q,J=7 cps 2H) for CH$_3$-CH$_2$-O- and 5.61 (M,2H) for —CH=CH—.

EXAMPLE 6

0.5 g. of potassium hydroxide are dissolved in 10 ml. of absolute ethanol and, together with 11.7 g. of 4-ethyl-2-hexenoic acid ethyl ester, cooled to about −40°C in an autoclave. 20 ml of condensed hydrogen sulphide are added to this mixture, the autoclave is immediately sealed and, after reaching room temperature, it is placed in an oil-bath of 70°C. After heating for 2 hours, it is again cooled to room temperature and worked up as in Examples 1–5. There are obtained 2.6 g. of pure 3-mercapto-4-ethyl-caproic acid ethyl ester of boiling point 63°/0.25 Hg, $n_D^{20}$ 1.4611.

The compound possesses a fatty-fruity odor with a slightly sulphurous side-note and in all is reminiscent of wine dregs.

4-ethyl-2-hexenoic acid ethyl ester is prepared by the reaction of 2-ethylbutanol with malonic acid followed by the esterification of the reaction product. The material has a boiling point of 85°C/11 mmHg, $n_D^{20}$ = 1.4419.

EXAMPLE 7

3.0 g. of 4-methyl-2-hexenoic acid 3'-cis-hexenyl ester is dissolved in 2 g. of 3-cis-hexenol in the presence of 0.2 g of sodium. The reaction mixture is treated with 10 ml. of liquid hydrogen sulfide in accordance with the procedures of foregoing Examples 1 –6.

Short path distillation yields 3-mercapto-4-methyl-caproic hex-3-enyl ester (0.7g.) mp 120°-0.5 mmHg $n_D^{20}$ 1.4731. The product is purified by preparative gas chromatography and possesses the following structural characteristics:

I.R. (cm-1), 2620, 1724, 1256, 1168, 744; NMR ($\delta$ in PPM): 0.91 and 0.975 (d and t, together 9H); 3.33 (m, 1H); 4.17 (t, 2H); 5.48 (m, 2H); MS(m/e at 70eV): 82 (basis = 100%), 83, 103, 115, 127, 145.

This compound possesses a green fruity smell reminiscent of apples.

The starting material may be obtained in the following manner:

280 q. malonic acid are dissolved in pyridine previously distilled over potassium hydroxide in a 1.5 liter4-necked flask equipped with stirrer, condenser, and thermometer. The reaction mixture is cooled and a mixture of 180 g. of 2-methylbutanal and 18 g. of piperidine added thereto. The mixture is heated under stirring to 90°C until evolution of carbon dioxide ceases. The mixture is then stirred for a further 12 hours. The reaction mixture is poured over ice and concentrated hydrochloric acid is added thereto to the Congo acid reaction. The reaction mixture is taken up in ether, the solvent removed by distillation and the residue distilled through a 25 cm. fractionation column packed with Raschig rings. The forerun is discarded, 4-methyl-2hexenoic acid distills at 118–120°/10 mmHg. $n_D^{20}$ = 1.4532. Yield: 94% = 225g.

232 g. of 4-methyl-2hexenoic acid, 380 ml. of absolute ethanol, and 23 g. of concentrated sulfuric acid are charged into a 1 liter round bottom flask equipped with condenser.

The mixture is heated under reflux for 12 hours, quenched with 500 ml. of water, and extracted with ether. The ether layer is washed twice with 10% aqueous sodium carbonate solution and with water, and the solvent removed by distillation. The residue is then distilled through a 25 cm. fractionation column packed with Raschig rings to yield 4-methyl-2-hexenoic acid ethyl ester b.p. 76°; $n_D^{20}$ = 1.4376.

20 g. of 4-methyl-2-hexenoic acid ethyl ester and 25 g. of 3-cis-hexenol are heated to boiling over 0.5 g. of anhydrous potassium carbonate under a Vigreux column. During the course of the esterification, the ethanol formed therein is distilled off through the column. After the reaction is completed, the reaction mixture is removed from the potassium carbonate by filtration and the 4-methyl-2hexenoic acid 3′-cis-hexenyl ester is fractionated under reduced pressure. There is obtained 20.9 g. of the ester, b.p. 90°–93° 0.25mmHg, $n_D^{20}$ = 1.4572.

EXAMPLE 8

In accordance with the foregoing Example, 5.6 g. of 4-methyl-2-hexenoic acid 2-hexenyl ester is reacted with 5 ml. of liquid hydrogen sulfide in the presence of 0.2 g. of azoisobutyronitrile. There is obtained a reaction product having a boiling point of approximately 105°/0.1mmHg. $n_D^{20}$ 1.4700, from which the pure 3-mercapto-4-methyl-caproic acid 2-hexenyl ester may be separated by means of preparative gas chromatography. The pure product has the following spectral characteristics:

I.R. ($\nu$ in cm$^-$): 2620, 1742, 1258, 1168, 980; NMR ($\delta$ in PPM): 0.85, 0.95; 0.975 (together 9H); 3.36; (m, 1H); 4.60 (d, 2H): 5.73 (m, 2H); MS (m/e): 55 (basis = 100%), 82, 83, 145, 127, 145, 201, 244.

The odor of the ester is green, pungent, sulfurous, and slightly earthy and mushroom like.

The starting material can be prepared in the following manner:

12.8 g. of 4-methyl-2-hexenoic acid and 17.5 g. of 2-hexenol are heated in the presence of 0.5 g. of p-toluene sulfonic acid and 25 ml. of chloroform under a condenser equipped with a Dean-Stark head. Heating is continued till no further water is seen to be liberated. After the cooled reaction product is washed with water and aqueous sodium bicarbonate solution, it is dried and the solvent is then removed by distillation. Distillation of the residue under reduced pressure yields 12.2 g. of 4-methyl-2-hexenoic acid 2-hexenyl ester. b.p. 104/1.4mmHg. $n_D^{20}$ = 1.4589.

EXAMPLE 9

10 grams of 4-methyl-2-hexenoic acid hexa-2,4-dienyl ester are treated with 0.4 g of sodium hydroxide in 10 ml of absolute ethanol in the presence of 0.1 g. hydroquinone. The reaction mixture charged to an autoclave and cooled to approximately −40°C in 12 ml. of liquid hydrogen sulfide added thereto. The autoclave is sealed and heated on an oil bath for 2 hours at 70°C. The autoclave is cooled, the excess pressure released, and the reaction mixture taken up in ether. The ether solution is washed to neutrality with water, dried and the solvent removed by distillation. The resiudal 3-mercapto-4-methyl-hexanoic acid hexa-2,4-dienyl ester (11.5 g.) is fractionated under reduced pressure, b.p. 110°/0.2 mmHg. $n_D^{20}$ 1.5035: IR: $\nu$ = 2580, 1734, 1660, 1160, 992 cm$^-$; U.V. $\lambda$ max 226.5nm ($\epsilon$ = 26,900). Odor: sulfurous having an onion or garlic-like tone.

The starting materials can be prepared in the following manner:

15.4 g. of 4-methyl-2-hexenoic acid are reacted with 21.6 g. of thionyl chloride to provide the corresponding acid chloride. The thus produced acid chloride is slowly, suitably dropwise, added to a solution of 11.4. g. of 2,4-hexadienol in 50 ml of absolute pyridine under cooling. After addition is complete, the reaction mixture is warmed for 20 minutes to 70°C and quenched by pouring over ice. The aqueous mixture is purified with dilute hydrochloric acid and the thus formed ester is taken up in ether. The ethereal solution is washed to neutrality, and the solvent removed by distillation. The residue is fractionated under reduced pressure to yield 12.2 g. of 4-methyl-2-hexenoic acid hexa-2,4-dienyl ester, b.p. 93°/0.3 mmHg, $n_D^{20}$ 1.4907.

EXAMPLE 10 by additions of 5-10 g. of a 10% solution of 3-mercapto-4-methyl-caproic acid ethyl ester, a carrier diluent composition of the lavender type containing

|  | Parts by weight |
|---|---|
| patchouli oil | 5 |
| coumarin | 5 |
| trans-bicyclo (10.1.0)tridec-1-yl methyl ether | 10 |
| rosemary oil - Spanish | 20 |
| p-tert.-butyl-cyclohexyl acetate | 40 |
| linalyl acetate | 80 |
| bergamotte oil Reggio | 100 |
| lavender oil Mont Blanc | 500 |
| lavandin 22/24 | 100 |
| rosewood oil acetylated | 50 |
| 4-docen-1-al (10% in phthalic acid diethyl ester) | 10 |
| lavandulal (10% in phthalic acid diethyl ester) | 40 |
| isobutylcitral | 20 |
| "Cistambral" Givaudan (10% in phthalic acid diethyl ester) | 20 |
|  | 1000 | is modified in a welcome manner in that the composition acquires a fruity-green aspect with a slightly grass-like reminiscence. Further, the addition brings about a marked fixation of the lavender character and imparts freshness and fullness to it.

EXAMPLE 11

An aqueous solution of the 3-mercapto-4-methyl-caproic acid ethyl ester (20 PPM) has a fruity, winey pineapply flavor having moderate to strong impact. The compound is useful in this concentration for flavoring fruits, meats, and in flavorant compositions.

We claim:

1. An odorant composition containing an olfactible amount of a compound having the general formula

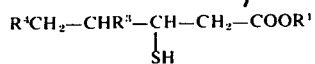

wherein R[1] is an alkyl group having 1 to 6 carbon atoms and is preferably unbranched, R[3] signifies hydrogen or alkyl containing 1-3 carbon atoms and R[4] signifies alkyl, preferably unbranched, containing 1-7 carbon atoms, and at least one fragrance material having a note selected from lavender, chypre, gardenia, jasmine and rose.

2. A composition according to claim 1, comprising between 20 and 1000 PPM of 3-mercapto-4-methyl-caproic acid ethyl ester.

3. A composition according to claim 1, including between 0.01 and 1% of said compound.

4. An odorant composition according to claim 1, comprising a carrier diluent composition of the lavender type containing 0.05 to 0.1 percent of 3-mercapto-4-methyl-caproic and ethyl ester.

* * * * *

UNITED STATES PATENT OFFICE
CERTIFICATE OF CORRECTION

Patent No. 3,948,816  Dated Apr. 6, 1976

Inventor(s) Daniel Helmlinger, et al

It is certified that error appears in the above-identified patent and that said Letters Patent are hereby corrected as shown below:

Column 8, line 10, "4-methyl-caproic and ethyl ester"
should read -- 4-methyl-caproic acid ethyl ester --.

Signed and Sealed this twenty-ninth Day of June 1976

[SEAL]

Attest:

RUTH C. MASON
Attesting Officer

C. MARSHALL DANN
Commissioner of Patents and Trademarks